United States Patent [19]
Reif et al.

[11] Patent Number: 5,969,162
[45] Date of Patent: Oct. 19, 1999

[54] PROCESS FOR PURIFYING PHTHALIDE

[75] Inventors: Wolfgang Reif, Frankenthal; Klemens Massonne, Westheim; Horst Neuhauser, Dudenhofen, all of Germany

[73] Assignee: BASF Aktiengesellschaft, Ludwigshafen, Germany

[21] Appl. No.: 09/202,482

[22] PCT Filed: Jun. 12, 1997

[86] PCT No.: PCT/EP97/03045

§ 371 Date: Dec. 16, 1998

§ 102(e) Date: Dec. 16, 1998

[87] PCT Pub. No.: WO98/00417

PCT Pub. Date: Jan. 8, 1998

[30] Foreign Application Priority Data

Jun. 27, 1996 [DE] Germany .......................... 196 25 693

[51] Int. Cl.⁶ .................................................. C07D 307/88
[52] U.S. Cl. ............................................................ 549/307
[58] Field of Search ................................................ 549/307

[56] References Cited

U.S. PATENT DOCUMENTS 4,178,295  12/1979  Englaender et al. ..................... 260/343

FOREIGN PATENT DOCUMENTS

| 2720929 | 11/1978 | Germany . |
| 28 03 319 | 8/1979 | Germany . |
| 2803319 | 8/1979 | Germany . |
| 3245544 | 6/1984 | Germany . |
| 32 45 544 | 6/1994 | Germany . |

*Primary Examiner*—Bernard Dentz
*Attorney, Agent, or Firm*—Keil & Weinkauf

[57] ABSTRACT

The disclosure is a process for purifying phthalide contaminated by carboxylic acids and/or their derivatives, which comprises adding polyethylene glycol and/or polypropylene glycol to the phthalide to be purified and then performing a fractional distillation.

10 Claims, No Drawings

PROCESS FOR PURIFYING PHTHALIDE

This application is a 371 of PCT/EP97/03045 filed Jun. 12, 1997.

The present invention relates to a process for purifying a phthalide contaminated by carboxylic acids, carboxylic anhydrides and/or carboxylic esters.

Various syntheses have been described for the preparation of phthalide starting from phthalic acid derivatives. In general, phthalide is prepared by selective hydrogenation of phthalic anhydride (DE-C-28 03 319).

The problem is generally the work-up and purification of the as-synthesized reaction products, since phthalide synthesis almost inevitably produces a crude product contaminated by carboxylic acids and their derivatives such as phthalic acid, phthalic anhydride, monomethyl phthalate, tetrahydrophthalide and 2-methylbenzoic acid. Removal of these by-products is very costly and sometimes not possible just by distillation.

It is known that phthalic anhydride and monomethyl phthalate in particular are not completely removable from phthalide by distillation. If the crude product contains phthalic acid, additional phthalic anhydride is formed during the distillation.

The problems with the removal of by-products mean that phthalide, the product of value, is obtained in only unsatisfactory yield and purity in a distillative work-up.

DE-C-32 45 544 discloses a process for distillative purification of phthalide contaminated by carboxylic acids by admixing the phthalide to be purified with n-butanol or isobutanol prior to the distillation and heating the mixture in an autoclave at between 150 and 280° C. for several hours before subjecting it to a fractional distillation. However, the disadvantages of this procedure are that it is very time-consuming and that excess butanol has to be distilled off prior to the distillation of the phthalide.

It is an object of the present invention to provide a simple and improved process for purifying phthalide essentially contaminated by carboxylic acids and their derivatives.

We have found that this object is advantageously achieved by a process for purifying phthalide contaminated by carboxylic acids, carboxylic anhydrides and/or carboxylic esters, which comprises adding polyethylene glycol and/or polypropylene glycol to the phthalide to be purified and then performing a fractional distillation.

In general, the polyethylene glycol and/or polypropylene glycol is or are added to the phthalide to be purified in amounts from 1 to 50% by weight, advantageously from 2 to 40% by weight, preferably from 3 to 30% by weight, especially from 5 to 15% by weight, particularly advantageously from 8 to 12% by weight, based on phthalide.

It is advantageous to use polyethylene glycol and polypropylene glycol whose average molar mass is within the range from 200 to 600, preferably within the range from 250 to 400.

The polyethylene glycols are advantageously obtained by polyaddition of ethylene oxide to ethylene glycol as initiator molecule in systems usually containing small amounts of water. The polypropylene glycols are formed in a corresponding manner by polyaddition of propylene oxide to 1,2-propanediol as initiator molecule.

It is an advantage of the process of the invention that, in general, even the addition of a relatively small amount of polyethylene glycol or polypropylene glycol to the crude phthalide product is sufficient for the purification process. It is a further advantage of the process that it is possible to dispense with a time-consuming thermal pretreatment of the admixture of crude phthalide and polyethylene glycol or polypropylene glycol. There is no need for prior heating, for example under reflux or in an autoclave. Accordingly, in a preferred embodiment of the purification process, the addition of polyethylene glycol or polypropylene glycol to the crude phthalide is followed by the fractional distillation directly, without further pretreatment. If the chemical structure and the molar mass of the polyethylene glycol or polypropylene glycol are selected in such a way that this ancillary component does not include anything which boils lower than phthalide, phthalide would be one of the low boilers in the distillation system. On application of this preferred procedure, unconverted polyethylene glycol or polypropylene glycol and their reaction products remain behind in the bottom product of the fractional distillation.

The phthalide obtained by the process of this invention is notable for particularly good purity and it is also obtained in good yield, the yield achieved being higher than the yield achieved via a distillation without addition of polyethylene glycol or polypropylene glycol. The polyethylene glycol or polypropylene glycol remaining behind in the bottom product also means that the bottom product remains liquid. This is advantageous, on the one hand, for the removal of the distillation residue from the distillation flask and, on the other, for a preferred procedure in which, after completion of each fractional distillation of crude phthalide to be purified, the distillation flask is repeatedly refilled with crude phthalide for another fractional distillation without the distillation residue from the preceding fractional distillation being removed.

Phthalide is an important intermediate, for example for the synthesis of crop protection agents.

The Examples which follow illustrate the invention.

INVENTIVE EXAMPLE 1

The fractional distillation was carried out using 1600 g of crude phthalide solution having approximately the following composition: 46.0% by weight of butyrolactone, 34.9% of phthalide, 15.0% by weight of water, 2.5% by weight of 2-methylbenzoic acid, 1.0% by weight of phthalic anhydride, 0.3% by weight of tetrahydrophthalide and 0.3% by weight of further by-products. This crude phthalide solution was admixed with 176 g (32% by weight, based on phthalide) of a polyethylene glycol having an average molar mass of 300. Then, without any further pretreatment, a fractional distillation was carried out using a laboratory column having 40 theoretical plates and a top-of-column pressure of 20 mbar. The distillation yield was 73% of phthalide in a purity of more than 98.5%.

The distillation residue was subsequently not removed for disposal, but it remained in the distillation flask. By repeatedly filling the flask with further crude phthalide solution and repeating the distillation, the total phthalide yield was increased to 87%. The phthalic anhydride content of the pure phthalide product was below 0.1%, and the 2-methylbenzoic acid content was below 0.2%.

INVENTIVE EXAMPLE 2

The fractional distillation was carried out similarly to Inventive Example 1, except that only 9% by weight, based on pthalide, of polyethylene glycol of the average molar mass of 300 was added to the crude phthalide solution prior to the distillation. The phthalide obtained in a yield of 87% had a purity of more than 98.5%, its phthalic anhydride content being below 0.1% and the 2-methylbenzoic acid content below 0.3%.

COMPARATIVE EXAMPLE

The fractional distillation was carried out using 1600 g of a crude phthalide solution of the same composition as in Inventive Example 1. The crude phthalide solution was distilled through a laboratory column having 40 theoretical plates using a top-of-column pressure of 20 mbar. The distillation yield was 58% of phthalide, obtained in a purity of 97.6% and with a phthalic anhydride content of 1.0%. A phthalide product of this purity is unsuitable for most applications.

We claim:

1. A process for purifying phthalide contaminated by carboxylic acids, carboxylic anhydrides and/or carboxylic esters, which comprises adding polyethylene glycol and/or polypropylene glycol to the phthalide to be purified and then performing a fractional distillation.

2. A process as claimed in claim 1, wherein the polyethylene glycol and/or polypropylene glycol added to the phthalide to be purified has an average molar mass within the range from 200 to 600.

3. A process as claimed in claim 1, wherein the polyethylene glycol and/or polypropylene glycol added to the phthalide to be purified has an average molar mass within the range from 250 to 400.

4. A process as claimed in claim 1, wherein the amount of polyethylene glycol and/or polypropylene glycol added to the phthalide to be purified is within the range from 1 to 50% by weight, based on phthalide.

5. A process as claimed in claim 1, wherein 2–40% by weight of polyethylene glycol is added.

6. A process as claimed in claim 1, wherein the fractional distillation is performed directly following addition of polyethylene glycol and/or polypropylene glycol to the phthalide to be purified and is not preceded by further pretreatment.

7. A process as claimed in claim 1, wherein the polyethylene glycol and/or polypropylene glycol added does not include anything which boils lower than phthalide.

8. A process as claimed in claim 1, wherein unconverted polyethylene glycol and/or polypropylene glycol remain behind in the bottom product of the fractional distillation and phthalide is distilled off as low boiler.

9. A process as claimed in claim 8, wherein, after each completed distillation, the bottom product remains behind in the distillation flask and the distillation flask is refilled with crude phthalide.

10. A process as claimed in claim 1, providing phthalide in a purity of more than 98.5%.

* * * * *